United States Patent [19]

Ikeda et al.

[11] Patent Number: 5,650,062
[45] Date of Patent: Jul. 22, 1997

[54] BIOSENSOR, AND A METHOD AND A DEVICE FOR QUANTIFYING A SUBSTRATE IN A SAMPLE LIQUID USING THE SAME

[75] Inventors: Shin Ikeda, Katano; Toshihiko Yoshioka, Osaka; Shiro Nankai, Hirakata; Haruhiro Tsutsumi, Ehime-ken; Hideyuki Baba, Matsuyama; Yoshinobu Tokuno, Matsuyama; Syoji Miyazaki, Matsuyama, all of Japan

[73] Assignee: Matsushita Electric Industrial Co., Ltd., Kadoma, Japan

[21] Appl. No.: 526,557

[22] Filed: Sep. 12, 1995

Related U.S. Application Data

[63] Continuation-in-part of Ser. No. 425,820, Apr. 20, 1995, Pat. No. 5,582,697.

[30] Foreign Application Priority Data

Mar. 17, 1995 [JP] Japan .................................. 7-58939

[51] Int. Cl.[6] .................................................. G01N 27/26
[52] U.S. Cl. ...................... 205/778; 205/775; 205/777.5; 204/403; 204/412; 204/415; 204/418; 435/817; 435/287.9; 435/287.1
[58] Field of Search ........................ 204/403, 412, 204/415, 418; 205/775, 778, 777.5; 435/817, 288, 291

[56] References Cited

U.S. PATENT DOCUMENTS

| | | | |
|---|---|---|---|
| 4,172,770 | 10/1979 | Semersky et al. | 204/412 |
| 5,192,415 | 3/1993 | Yoshioka et al. | 204/403 |
| 5,264,103 | 11/1993 | Yoshioka et al. | 204/403 |

FOREIGN PATENT DOCUMENTS

| | | |
|---|---|---|
| 0359831 | 3/1990 | European Pat. Off. . |
| 0502504 | 9/1992 | European Pat. Off. . |
| 0537761 | 4/1993 | European Pat. Off. . |
| 4115795 | 11/1992 | Germany . |

OTHER PUBLICATIONS

Search Report for European Appl. 95110746.5, Mailed Jul. 19, 1996.

*Primary Examiner*—Bruce F. Bell
*Attorney, Agent, or Firm*—Renner, Otto, Boisselle & Sklar

[57] ABSTRACT

The biosensor of this invention can quantify a substrate in a sample liquid by electrochemically measuring the amount of an electron acceptor that has been reduced by electrons generated in a reaction between the substrate and an oxidoreductase. The biosensor has an electrically insulating substrate and an electrode system formed on the substrate including a working electrode, a counter electrode and a third electrode used for detecting a liquid junction. The third electrode can be used merely for detecting a liquid junction, or can be used as both a reference electrode and a liquid junction detecting electrode.

13 Claims, 4 Drawing Sheets

BIOSENSOR, AND A METHOD AND A DEVICE FOR QUANTIFYING A SUBSTRATE IN A SAMPLE LIQUID USING THE SAME

This application is a continuation-in-part of U.S. patent application Ser. No. 08/425,820 filed Apr. 20, 1995, now U.S. Pat. No. 5,582,697.

BACKGROUND OF THE INVENTION

1. Field of the Invention

The present invention relates to a biosensor that can easily quantify a substrate (a specific component) in a sample liquid with speed and accuracy, and to a method and a device for quantifying a substrate by using the biosensor. More particularly, the invention relates to a biosensor that can quantify a substrate in a sample liquid by electrochemically measuring the amount of an electron acceptor that has been reduced with an electron generated in a reaction between the substrate in the sample liquid and an oxidoreductase that specifically reacts with the substrate, and to a method and a device for quantifying a substrate by using the biosensor.

2. Description of the Related Art

The optical rotation method, the colorimetric method, the reductimetry method and other methods using different kinds of chromatographies have been developed as methods for quantitative analysis of saccharides such as sucrose and glucose. However, none of these methods can provide high accuracy due to the relatively low specificity against saccharides. Among these methods, the optical rotation method is easy to operate but is largely influenced by the operating temperature. Therefore, it is not appropriate for common use at home and the like.

Various types of biosensors utilizing a specific catalysis of an enzyme have been recently developed. As an example of methods for quantifying a substrate in a sample liquid, a method for quantifying glucose will now be described. For electrochemically quantifying glucose, a method using glucose oxidase (EC1.1.3.4; hereinafter referred to as GOD) and an oxygen electrode or a hydrogen peroxide electrode is generally known (for example, "Biosensor" edited by Shuichi Suzuki, Kodansha Kabushiki Kaisha).

GOD selectively oxidizes β-D-glucose into D-glucono-δ-lactone by using oxygen as an electron acceptor. In an oxidation reaction using GOD in the presence of oxygen, oxygen is reduced to hydrogen peroxide. In the aforementioned method, the amount of reduced oxygen is measured by using an oxygen electrode, or the amount of increased hydrogen peroxide is measured by using a hydrogen peroxide electrode. Since the amounts of the reduced oxygen and the increased hydrogen peroxide are in proportion to the content of glucose in the sample liquid, glucose can be quantified based on the amount of the reduced oxygen or the increased hydrogen peroxide.

The above-mentioned method, however, has a problem in that the measurement result is largely affected by the concentration of oxygen in the sample liquid, as can be presumed from the reaction process. Furthermore, when no oxygen is contained in the sample liquid, the above-mentioned method cannot be adopted.

In order to solve this problem, a new type of glucose sensor has been developed, in which an organic compound such as potassium ferricyanide, a ferrocene derivative and a quinone derivative or a metal complex is used as an electron acceptor instead of oxygen. In this type of sensor, the reduced form of an electron acceptor resulting from the enzymatic reaction is oxidized on an electrode, and the concentration of glucose contained in a sample liquid is obtained based on the amount of the measured oxidation current. By using an organic compound or a metal complex as an electron acceptor instead of oxygen, it is possible to hold a known amount of GOD and its electron acceptor on an electrode stably and accurately, so as to form a reaction layer. In this case, the reaction layer can be integrated with the electrode in a substantially dry state. Therefore, a disposable glucose sensor based on this technique has recently come to public notice. In this disposable glucose sensor, the concentration of glucose in a sample liquid can be easily measured with a measuring device merely by introducing the sample liquid into the sensor removably connected to the measuring device. Such a method can be applied not only to the quantification of glucose but also to the quantification of any other substrate contained in a sample liquid.

When a substrate in a sample liquid is quantified by such a method, a two-electrode system sensor having a working electrode and a counter electrode is generally used.

In the measurement using such a two-electrode system sensor, before applying a voltage between the working electrode and the counter electrode to obtain a current response, a voltage is generally applied between the working electrode and the counter electrode so as to detect a liquid junction based on the change of a resistance value between these electrodes. In such a case, the interface between the electrodes can be varied by the application of the voltage, resulting in affecting the measurement. Furthermore, the resistance value between the working electrode and the counter electrode can be sometimes varied to start the measurement before supplying a sufficient amount of a sample liquid to the electrode system. This also affects the measurement.

SUMMARY OF THE INVENTION

The biosensor of this invention quantifies a substrate in a sample liquid by electrochemically measuring an amount of an electron acceptor that has been reduced by electrons generated in a reaction between the substrate and an oxidoreductase. The biosensor comprises an electrically insulating substrate, an electrode system formed on the substrate including a working electrode, a counter electrode and a third electrode used for detecting a liquid junction, and a reaction layer that is formed over at least the working electrode and the counter electrode of the electrode system and includes the oxidoreductase.

In one embodiment, the third electrode is disposed farther from a sample supply port than the working electrode and the counter electrode, so that a sample liquid supplied through the sample supply port reaches the third electrode after reaching the working electrode and the counter electrode.

In another embodiment, the third electrode is disposed nearer to a sample supply port than the counter electrode, so that a sample liquid supplied through the sample supply port reaches the third electrode before reaching the working electrode.

In another embodiment, the counter electrode includes a main electrode portion formed in substantially a C-shape in a plane view and an opening formed in the main electrode portion, the working electrode disposed inside of the counter electrode so as to be electrically insulated from each other, and a lead connected to the working electrode is led from the inside to the outside of the counter electrode through the opening.

In another embodiment, a peripheral portion of the counter electrode is opened to provide an electrode receiving portion, and the third electrode is disposed within the electrode receiving portion.

In another embodiment, the counter electrode includes a main electrode portion formed In substantially a C-shape in a plane view and an opening formed in the main electrode portion, the working electrode disposed inside of the counter electrode so as to be electrically insulated from each other, a lead connected to the working electrode is led from the inside to the outside of the counter electrode through the opening, and the third electrode is disposed between the counter electrode and the working electrode so as to be electrically insulated from one another.

In another embodiment, the reaction layer is formed also over the third electrode.

In another embodiment, a cover is provided over the substrate, and a space serving as a sample supply path is formed between the substrate and the cover.

In another embodiment, the electrode system is exposed to the space.

In another embodiment, the reaction layer further includes an electron acceptor.

In another embodiment, the reaction layer further includes a hydrophilic polymer.

The method for quantifying a substrate in a sample liquid of this invention uses the aforementioned biosensor. This method comprises the steps of applying a voltage between the counter electrode and the third electrode, supplying a sample liquid to the reaction layer, detecting an electrical change between the counter electrode and the third electrode caused by supplying the sample liquid to the reaction layer, applying a voltage between the working electrode and both of the third electrode and the counter electrode or the counter electrode after detecting the electrical change, and measuring a current flowing between the counter electrode and the working electrode after applying the voltage.

The quantifying device for a substrate contained in a sample liquid of this invention comprises the aforementioned biosensor, means for detecting an electrical change between the counter electrode and the third electrode caused by supplying a sample liquid to the reaction layer, means for applying a voltage between the working electrode and both of the third electrode and the counter electrode or the counter electrode after detecting the electrical change, and means for measuring a current flowing between the working electrode and the counter electrode.

In another embodiment, the quantifying device for a substrate contained in a sample liquid, includes the aforementioned biosensor and a measuring device removably connected to the biosensor. In this device, the measuring device includes: current/voltage converting circuits connected to the third electrode of the biosensor; A/D converting circuits connected to the current/voltage converting circuits; current/voltage converting circuits capable of being connected to the working electrode of the biosensor via a switch; A/D converting circuits connected to the current/voltage converting circuits; and a controller connected to the respective A/D converting circuits, the switch being turned ON or OFF with respect to the working electrode by a control of the controller. Also in this device, an electrical change between the counter electrode and the third electrode, caused by a supply of a sample liquid to the reactive layer, is detected by the control portion under a condition that the switch is insulated from the working electrode, and then a voltage is applied between the working electrode and both of the third electrode and the counter electrode or the counter electrode under a condition that the switch is connected to the working electrode and a current flowing between the working electrode and the counter electrode as measured.

In another embodiment, the quantifying device for a substrate contained in a sample liquid, includes the aforementioned biosensor and a measuring device removably connected to the biosensor. In this device, the measuring device includes: current/voltage converting circuits switchably connected to the third electrode of the biosensor and the working electrode; A/D converting circuits connected to the current/voltage converting circuits; a controller connected to the respective A/D converting circuits, the switch being alternatively connected to the working electrode and the third electrode by a control of the controller. Also in this device, an electrical change between the counter electrode and the third electrode, caused by a supply of a sample liquid to the reactive layer, is detected by the control portion under a condition that the switch is connected to the third electrode, and then a voltage is applied between the working electrode and the counter electrode under a condition that the switch is connected to the working electrode and a current flowing between the working electrode and the counter electrode measured.

Thus, the invention described herein makes possible the advantages of (1) providing a biosensor that can easily quantify a specific substrate in a sample liquid with speed and accuracy; (2) providing a biosensor in which the interface between a counter electrode and a working electrode is not varied in detecting a liquid junction, so that the detection of the liquid junction does not affect the measurement; (3) providing a biosensor in which a potential at a counter electrode used as a reference is not varied by an oxidation/reduction reaction at a working electrode, so as to decrease errors and deviation in the measurement; and (4) providing a biosensor that can quantify saccharides in fruit or saccharides in blood, lymph, urine and saliva or other body fluids.

These and other advantages of the present invention will become apparent to those skilled in the art upon reading and understanding the following detailed description with reference to the accompanying figures.

DESCRIPTION OF THE PREFERRED EMBODIMENTS

A biosensor of this invention comprises an electrically insulating substrate, an electrode system that is formed on the substrate and includes a working electrode, a counter electrode and a third electrode, and a reaction layer formed over the working electrode and the counter electrode of the electrode system. The working electrode, the counter electrode and the third electrode of the electrode system are preferably formed on the same plane on the substrate.

The electrically insulating substrate can be formed from a plate made of a synthetic resin such as polyethylene terephthalate or any other suitable resin known in the art.

The electrode system including the working electrode, the counter electrode corresponding to the working electrode and the third electrode can be formed on the substrate by a known method. For example, after forming leads on the substrate, the working electrode, the counter electrode and the third electrode are formed so as to be connected to the respective leads and be insulated from one another. The material for the leads and the electrodes can be of any known conductive materials such as silver paste and carbon paste. Furthermore, a silver/silver chloride electrode can be used.

The shapes and the positions of the respective electrodes of the electrode system can be variously modified. For example, the counter electrode can be in the shape of a ring or be substantially a C-shape in a plane view. The working electrode can be positioned in a space within the ring-shaped or C-shaped counter electrode so as to be electrically insulated therefrom. By providing the working electrode inside of the counter electrode, these electrodes can be positioned adjacent to each other. In this case, the reaction layer covering the working electrode and the counter electrode can be easily formed.

When the counter electrode is formed so as to have a substantially C-shaped main electrode portion and an opening formed in the main electrode portion, a lead connected to the working electrode positioned inside of the main electrode portion is led from the inside to the outside of the main electrode portion through the opening.

In a peripheral portion of the counter electrode can be formed an electrode receiving portion for the third electrode. The shapes of the electrode receiving portion and the third electrode can be variously modified according to the required application. Furthermore, the position of the electrode receiving portion in the counter electrode can be varied depending upon the application of the biosensor.

For example, the third electrode can be positioned farther from a sample supply port of the biosensor than the working electrode and the counter electrode, so that a sample liquid supplied through the sample supply port can reach the third electrode after reaching the working electrode and the counter electrode. Alternatively, the third electrode can be positioned nearer to the sample supply port than the working electrode, so that a sample liquid supplied through the sample supply port can reach the third electrode before reaching the working electrode and the counter electrode.

When the third electrode is positioned farther from the sample supply port than the working electrode and the counter electrode, the change of a resistance value between the counter electrode and the third electrode cannot be detected until a space including all of the three electrodes is filled with a sample liquid. Accordingly, by utilizing such a third electrode for detecting a liquid junction, it can be definitely determined whether or not a sample liquid supplied through the sample supply port has covered the entire reaction layer.

To the contrary, when the third electrode is positioned nearer to the sample supply port than the working electrode and the counter electrode, the third electrode is soaked with the supplied sample liquid without fail. Accordingly, by utilizing such a third electrode as a reference electrode, a reference potential can be more stabilized, resulting in attaining a measurement having less deviation.

The third electrode can also be positioned between the counter electrode and the working electrode so as to be electrically insulated therefrom.

The reaction layer can be formed over the working electrode and the counter electrode of the electrode system. Alternatively, the reaction layer can be formed over not only the working electrode and the counter electrode but also the third electrode.

The reaction layer can be formed with one layer or two layers including at least an enzyme (oxidoreductase), and more preferably further including an electron acceptor. When the reaction layer is formed with two layers, the two layers can be a first layer made of a hydrophilic polymer formed directly on the electrode system, and a second layer including at least an enzyme and an electron acceptor laminated on the first layer.

Examples of the hydrophilic polymer forming the first hydrophilic polymer layer include carboxy methyl cellulose (hereinafter referred to as CMC), hydroxyethyl cellulose (hereinafter referred to as HEC), hydroxypropyl cellulose (hereinafter referred to as HPC), methyl cellulose, ethyl cellulose, ethyl hydroxyethyl cellulose, carboxymethyl ethyl cellulose, polyvinyl pyrrolidone, polyvinyl alcohol, polyamino acids such as polylysine, polystyrene sulfonate, gelatin or its derivative, acrylic acid or its salt, methacrylic acid or its salt, starch or its derivative, and maleic anhydride or its salt. Among the above, CMC, HEC, HPC, methyl cellulose, ethyl cellulose, ethyl hydroxyethyl cellulose and carboxymethyl ethyl cellulose are preferred.

The kind of oxidoreductase contained in the reaction layer depends upon a substrate contained in a sample liquid to be quantified and is not herein specifically defined. Examples of the oxidoreductase include fructose dehyrogenase, invertase, mutarotase, glucose oxidase, alcohol oxidase, lactic acid oxidase, cholesterol oxidase, xanthine oxidase and amino acid oxidase.

Examples of the electron acceptor include potassium ferricyanide, p-benzoquinone, phenazine methosulfate, methylene blue and a ferrocene derivative. One or a combination of two or more of the above can be used as the electron acceptor.

The enzyme end the electron acceptor can be dissolved in a sample liquid, or the reaction layer is immobilized on the substrate or the like so as not to allow the enzyme and the electron acceptor to dissolve in a sample liquid. When the enzyme and the electron acceptor are immobilized, the reaction layer preferably includes the hydrophilic polymer.

The reaction layer can further include a pH buffer such as potassium dihydrogenphosphate—dipotassium hydrogenphosphate, potassium dihydrogenphosphate—disodium hydrogenphosphate, sodium dihydrogenphosphate dipotassium hydrogenphosphate, sodium dihydrogenphosphate—disodium hydrogenphosphate, citric acid—disodium hydrogenphosphate, citric acid—dipotassium hydrogenphosphate, citric acid—sodium citrate, citric acid—potassium citrate, potassium dihydrogencitrate—sodium hydroxide, sodium dihydrogencitrate—sodium hydroxide, sodium hydrogenmaleate—sodium hydroxide, potassium hydrogenphthalate—sodium hydroxide, succinic acid—sodium tetraborate, maleic acid—tris(hydroxymethyl) aminomethane, tris(hydroxymethyl) aminomethane—tris(hydroxymethyl)aminomethanehydrochloride, [N-(Z-hydroxyethyl)piperazine-N'-2-ethanesulfonic acid]—sodium hydroxide, [N-tris(hydroxymethyl)methyl-2-aminoethanesulfonic acid]—sodium hydroxide, and [piperazine-N,N'-bis(2-ethanesulfonic acid)]—sodium hydroxide.

The reaction layer can be formed by dropping on a substrate a solution including at least the enzyme and more preferably further including the electron acceptor and drying the dropped solution.

When the reaction layer is formed with the first hydrophilic polymer layer and the second layer that includes the enzyme and the electron acceptor and is laminated on the first layer, the second layer can be formed by, for example, dropping a mixed solution of the enzyme and the electron acceptor on the first layer.

Now, a method for quantifying a substrate in a sample liquid by using the biosensor will be described.

Figure 7:
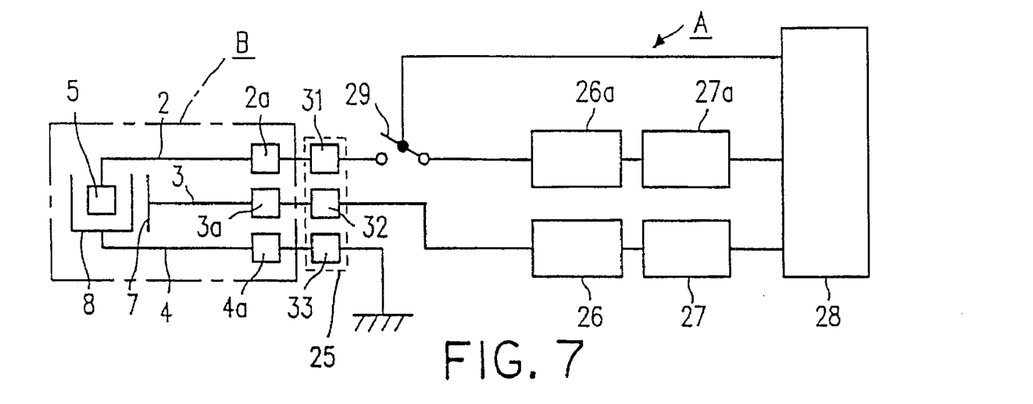
FIG. 7 is an exemplified circuit diagram for the biosensor of this invention and a measuring device connected thereto.
Figure 8:
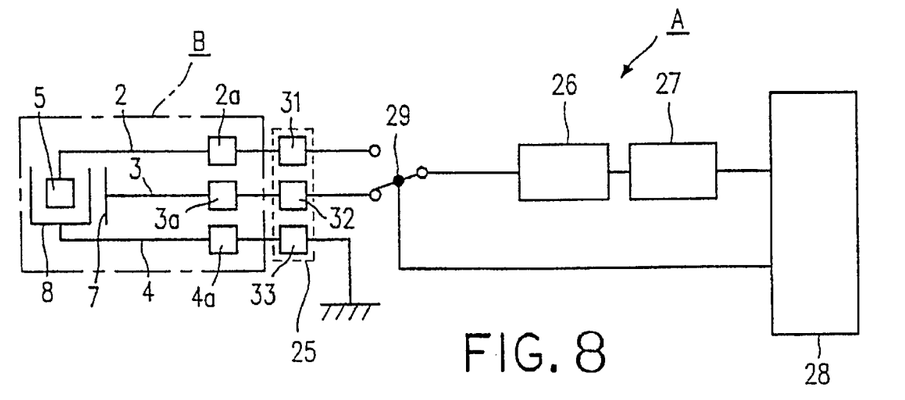
FIG. 8 is another exemplified circuit diagram for the biosensor of this invention and a measuring device connected thereto.

The method can be carried out with a quantifying device comprising a measuring device A and the biosensor B removably connected to the measuring device A as is shown in FIG. 7 or 8.

As is shown in FIGS. 7 and 8, the biosensor B comprises an electrode system formed on a substrate including a working electrode 5, a counter electrode 8 and a third electrode 7 used for detecting a liquid Junction. The working electrode 5 is connected to a terminal 2a via a lead 2. The counter electrode 8 is connected to a terminal 4a via a lead 4. The third electrode 7 is connected to a terminal 3a via a lead 3. The measuring device A shown in FIG. 7 comprises a connector 25 including terminals 31, 32 and 33 connected to the respective terminals 2a, 3a and 4a of the biosensor B, current/voltage converting circuits 26 connected to the terminal 32 of the connector 25, A/D converting circuits 27 connected to the respective current/voltage converting circuits 26, current/voltage converting circuits 26a connected to the terminal 31 via a switch 29, A/D converting circuits 27a connected to the respective current/voltage converting circuits 26a, and a controller 28 including a microcomputer and the like connected to the respective A/D converting circuits 27 and 27a. The above-mentioned switch 29 is ON/OFF controlled by the controller 28.

An operation of a circuit including the biosensor B and the measuring device A of FIG. 7 will be described.

First, the biosensor B is connected to the measuring device A. At this time, the switch 29 is disconnected from the terminal 31 by the controller 28. On the other hand, a predetermined voltage (e.g., 0.5 volts) is applied between the counter electrode 8 and the third electrode 7. When a sample liquid is supplied to the biosensor B under this condition, a current flows between the counter electrode 8 and the third electrode 7. The value of this current is detected by the controller 28. Based on this detection, a time is measured. After a predetermined period of time, the switch 29 is switched to the terminal 31 and a predetermined voltage (e.g., 0.5 volts) is applied to the working electrode 5. A fixed voltage (e.g., 0.5 volts) required for obtaining a response current is applied between the working electrode 5 and the counter electrode 8 of the biosensor B. A current thus flowing between the working electrode 5 and the counter electrode 8 is converted into a voltage by the current/voltage converting circuits 26a, and the obtained voltage value is converted into the number of pulses in a fixed period of time by the A/D converting circuits 27a. The controller 28 counts up the number of the pulses, calculates a response value, and indicates the result.

Therefore, when a sample liquid including a substrate (for example, a saccharide) is supplied to the biosensor B, the reaction layer is dissolved in the sample liquid. After a predetermined period of time from the supply of the sample liquid, a fixed voltage is applied between the working electrode 5 and the counter electrode 8. Then, after a predetermined period of time, a current value of a current flowing through the electrodes is measured. The obtained current value is in proportion to the concentration of the substrate in the sample liquid. A large number of current values are previously measured with regard to a plurality of sample liquids including the substrate at various known concentrations so as to obtain the relationship between the concentration and the current value. Then, the substrate contained in a sample liquid at an unknown concentration can be quantified by measuring a current value as described above.

In such a quantifying method in which the change of the concentration of a substrate caused through the reaction between an enzyme and the substrate in a sample liquid is measured based upon an electrochemical response obtained by applying a voltage to the working electrode 5, when the third electrode 7 is used, as a reference electrode, in addition to the working electrode 5 and the counter electrode 8, the deviation of a reference potential can be substantially ignored.

Furthermore, when the third electrode 7 is used for detecting a liquid junction, even though there is no need to apply a voltage between the working electrode 5 and the counter electrode 8 for the detection of the liquid junction as is conventionally applied, the supply of the sample liquid can be detected without fail. Furthermore, when the third electrode 7 is commonly used as a reference electrode and a liquid junction detecting electrode, the structure of the electrode system can be simplified.

The measuring device A shown in FIG. 8 comprises a connector 25 including terminals 31, 32 and 33 connected to the respective terminals 2a, 3a and 4a of the biosensor B, current/voltage converting circuits 26 connected to the respective terminals 31 or 32 of the connector 25 via a switch 29, A/D converting circuits 27 connected to the respective current/voltage converting circuits 26, a controller 28 including a microcomputer and the like connected to the respective A/D converting circuits 27. The above-mentioned switch 29 is ON/OFF controlled by the controller 28.

An operation of a circuit including the biosensor B and the measuring device A of FIG. 8 will be described.

First, the biosensor B is connected to the measuring device A. At this time, the switch 29 is connected to the terminal 32 by the controller 28. A predetermined voltage (e.g., 0.5 volts) is applied between the counter electrode 8 and the third electrode 7. When a sample liquid is supplied to the biosensor B under this condition, a current flows between the counter electrode 8 and the third electrode 7. The value of this current is detected by the controller 28. Based on this detection, a time is measured. After a predetermined period of time, the switch 29 is switched to the terminal 31 and a predetermined voltage (e.g., 0.5 volts) is applied to the working electrode 5; A fixed voltage (e.g., 0.5 volts) required for obtaining a response current is applied between the working electrode 5 and the counter electrode 8 of the biosensor B.

A current thus flowing between the working electrode 5 and the counter electrode 8 is converted into a voltage by the current/voltage converting circuits 26, and the obtained voltage value is converted into the number of pulses in a fixed period of time by the A/D converting circuits 27. The controller 28 counts up the number of the pulses, calculates a response value, and indicates the result.

In the measuring device shown in FIG. 7, a voltage can be applied between the working electrode 5 and the counter electrode 8 or between the working electrode 5 and both of the third electrode 7 and the counter electrode 8, while a voltage is continuously applied between the counter electrode 8 and the third electrode 7.

The measuring device A shown in FIG. 7 requires the current/voltage converting circuits 26 and 26a, and the A/D converting circuits 27 and 27a, respectively for the working electrode 5 and the counter electrode 8. In the measuring device A shown in FIG. 8, the current/voltage converting circuits 26 and the A/D converting circuits 27 can be commonly used for the working electrode 5 and the counter electrode 8.

The application of the biosensor of this invention depends upon a substrate (a specific component) in a sample liquid to be quantified. The biosensor can be used as, for example, a fructose sensor, a sucrose sensor, a glucose sensor, an alcohol sensor, a lactic acid sensor, a cholesterol sensor and an amino acid sensor.

EXAMPLES

Throughout the drawings mentioned in the following description, the same element has a common reference numeral, and the description is omitted as occasion demands.

Example 1

Figure 1:
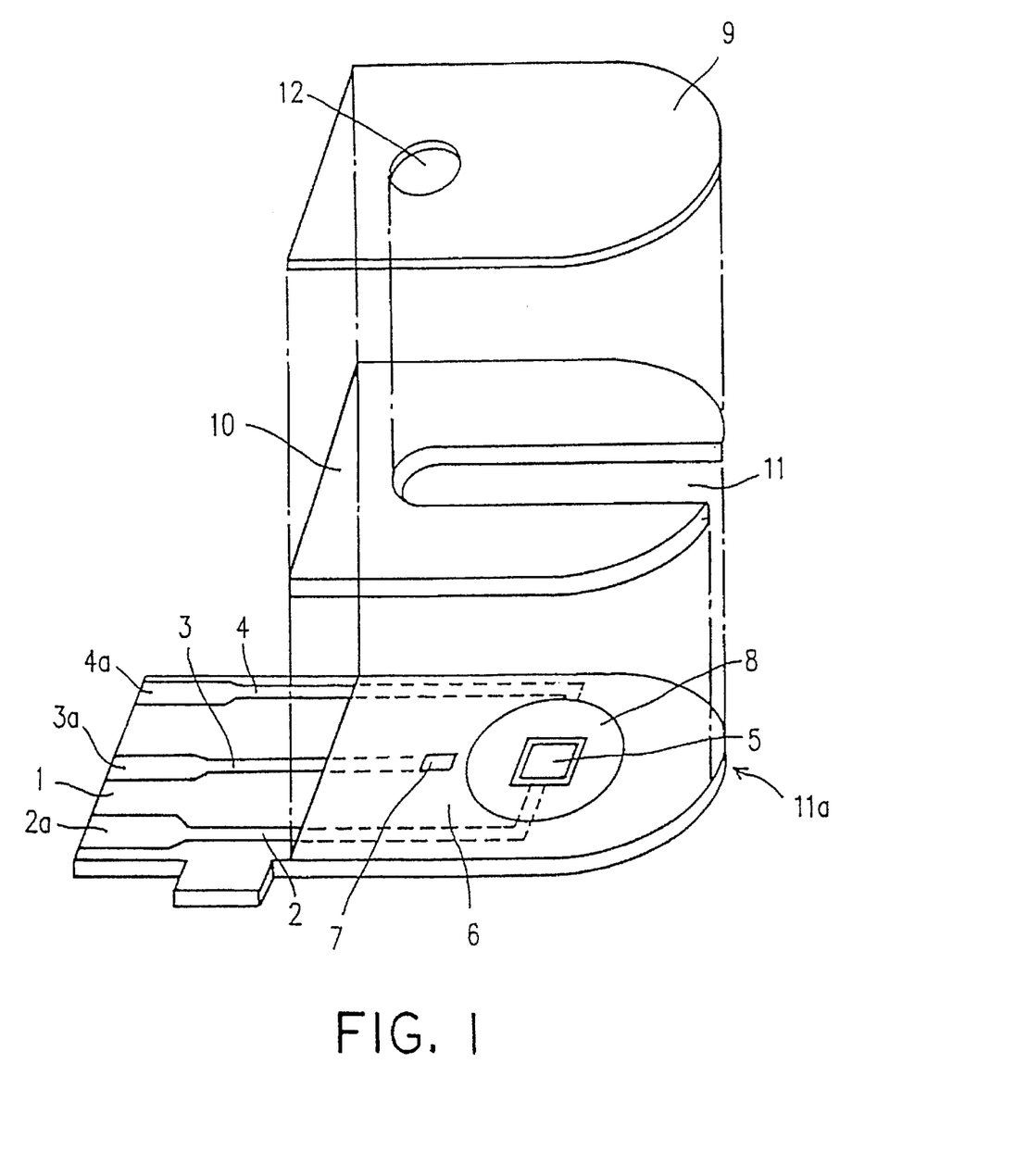
FIG. 1 is an exploded perspective view of a glucose sensor as an example of a biosensor of this invention from which a reaction layer is removed.

In this example, a method for quantifying glucose will be described. A glucose sensor shown in FIG. 1 was used. FIG. 1 is an exploded perspective view of a glucose sensor from which a reaction layer is removed. The glucose sensor comprises an insulating substrate 1 made of polyethylene terephthalate, a cover 9, and a spacer 10 sandwiched between the substrate 1 and the cover 9. The substrate 1, the spacer 10 and the cover 9 are adhered to one another in the positional relationship as is shown with broken lines in FIG. 1, thereby forming the glucose sensor.

A sample supply port 11 is formed in the spacer 10, and an air port 12 is formed in the cover 9. When the cover 9 is adhered to the substrate 1 with the spacer 10 interposed therebetween, the substrate 1, the spacer 10 and the cover 9 form a space (not shown) communicated with the sample supply port 11, and the end portion of the space is communicated with the air port 12.

On the substrate 1 are formed a working electrode 5, a third electrode 7, a counter electrode 8, and leads 2, 3 and 4 electrically connected to these electrodes, respectively. The working electrode 5 is positioned inside of the counter electrode 8 which has a ring shape. The third electrode 7 is positioned farther from an inlet 11a of the sample supply port 11 than the working electrode 8. Over the electrode system excluding the third electrode 7 (i.e., the working electrode 5 and the counter electrode 8) is formed a reaction layer (not shown). A reference numeral 6 in FIG. 1 denotes an insulating layer.

The working electrode 5, the counter electrode 8 and the third electrode 7 are exposed to the abovementioned space.

This glucose sensor was manufactured as follows:

Silver paste was printed by screen printing on the insulating substrate 1 made of polyethylene terephthalate, thereby forming the leads 2, 3 and 4. Then, conductive carbon paste including a resin binder was printed on the substrate 1, thereby forming the working electrode 5 so as to be in contact with the lead 2.

Next, insulating paste was printed on the resultant substrate 1, thereby forming the insulating layer 6. The insulating layer 6 covered the peripheral of the working electrode 5, so as to expose a fixed area of the working electrode 5. The insulating layer 6 also covered part of the leads 2, 3 and 4. The third electrode 7 was formed by exposing an end of the lead 3.

Then, conductive carbon paste including a resin binder was printed on the resultant substrate 1, thereby forming the counter electrode 8 so as to be in contact with the lead 4.

Next, an aqueous solution of CMC was dropped on the electrode system excluding the third electrode 7 (i.e., the working electrode 5 and the counter electrode 8) to be dried, thereby forming a CMC layer. Furthermore, an aqueous solution including GOD as an enzyme and potassium ferricyanide as an electron acceptor was dropped on the electrode system excluding the third electrode 7 (i.e., the working electrode 5 and the counter electrode 8) to be dried. Thus, the reaction layer was formed.

In order to attain a smoother supply of a sample liquid to the reaction layer, an organic solvent solution of lecithin (for example, a toluene solution) was spread from the inlet 11a of the sample supply port 11 over the entire reaction layer to be dried, thereby forming a lecithin layer. After this, the substrate 1, the cover 9 and the spacer 10 were adhered to one another as is shown with the broken lines in FIG. 1. The glucose sensor was thus manufactured.

The glucose sensor was supplied with 3 µl of an aqueous solution of glucose as a sample liquid through the sample supply port 11. The sample liquid reached the air port 12 through the space, and the reaction layer on the electrode system was dissolved therein.

Simultaneously with the supply of the sample liquid, a system for detecting the supply of a sample liquid based on the change of a resistance value between the counter electrode 8 and the third electrode 7 was operated, thereby actuating the measurement timer. After 55 seconds, a desired potential on the basis of the potential at the third electrode 7 was applied to the working electrode 5, and after 5 seconds, a current value was measured. A reaction is effected among ferricyanide ions, glucose and GOD in the sample liquid, resulting in the oxidation of glucose into glucono lactone and reduction of the ferricyanide ions into ferrocyanide ions. A current response can be obtained by oxidizing the ferrocyanide ions. In this manner, a current value depending upon the concentration of glucose in the sample liquid was obtained.

While applying the potential to the working electrode 5, the potential at the third electrode 7 was measured on the basis of a silver/silver chloride electrode. As a result, it was found that the potential at the third electrode 7 was scarcely varied although an oxidation reaction was effected in the working electrode 5. Furthermore, the response characteristic was found to be improved in this method as compared with the conventional method in which the liquid junction is detected based on the change of a resistance value between the working electrode and the counter electrode.

Since the third electrode 7 is positioned farthest from the inlet 11a of the sample supply port 11 in this example, a change of the resistance value between the counter electrode 8 and the third electrode 7 cannot be detected until the space including all the three electrodes is filled with the sample liquid. Accordingly, it can be definitely determined whether or not the sample liquid supplied through the sample supply port 11 has covered the entire reaction layer.

In this example, the case where the reaction layer is not formed over the third electrode 7 is described, but also when a reaction layer was formed over the third electrode 7, the same result was obtained.

Furthermore, the biosensor with the cover 9 is described in this example, but also when a biosensor without the cover 9 was used, a sensor response depending upon the concentration of glucose was obtained.

Example 2

Figure 2:
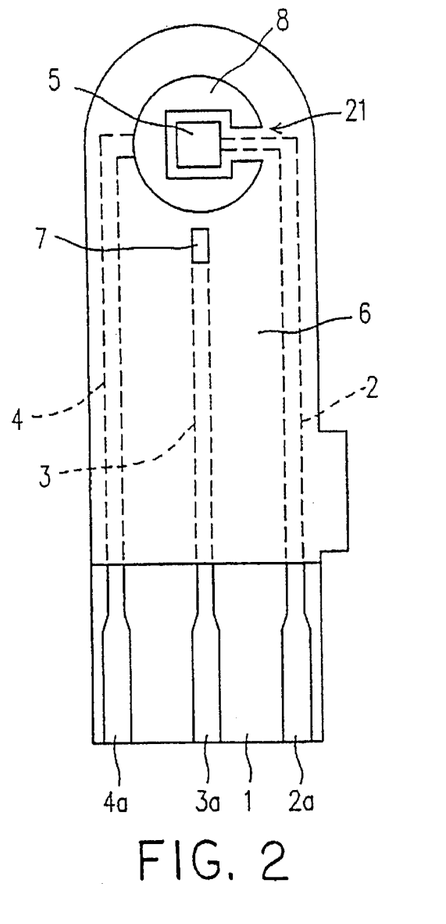
FIG. 2 is a plane view of a substrate having an electrode system used in a glucose sensor as another example of the biosensor of this invention.

The electrode system of a glucose sensor used in this example is shown in FIG. 2.

In this glucose sensor, a counter electrode 8 formed on a substrate 1 includes a substantially C-shaped main electrode portion and an opening 21 formed in the main electrode portion. A lead 2 connected to a working electrode 5 is led from the inside to the outside of the counter electrode 8 through the opening 21. The configuration of the glucose sensor is substantially identical to that of Example 1 except for the above.

This glucose sensor was manufactured as follows:

Silver paste was printed by screen printing on the insulating substrate 1 made of polyethylene terephthalate, thereby forming the leads 2, 3 and 4. Then, conductive carbon paste including a resin binder was printed on the substrate 1, thereby forming the working electrode 5 and the counter electrode 8 so as to be in contact with the leads 2 and 4, respectively.

Next, insulating paste was printed on the resultant substrate 1, thereby forming an insulating layer 6. The insulating layer 6 covered the peripheral of the working electrode 5, so as to expose a fixed area of the working electrode 5. The insulating layer 6 also covered part of the leads 2, 3 and 4. A third electrode 7 was formed by exposing an end of the lead 3.

The manufacturing procedures thereafter were identical to those in Example 1.

The glucose sensor was supplied with 3 µl of an aqueous solution of glucose as a sample liquid through the sample supply port 11 in the same manner as in Example 1, and a response current value was measured. As a result, it was also definitely determined whether or not the sample liquid had covered the entire reaction layer.

Since the lead 2 connected to the working electrode 5 is led from the inside to the outside of the counter electrode 8 through the opening 21 thereof in this example, the working electrode 5 and the counter electrode 8 can be simultaneously formed on the substrate 1 by the printing. Accordingly, the number of manufacturing procedures is decreased by one as compared with Example 1, and hence, the production cost of the biosensor can be reduced.

Example 3

A glucose sensor was manufactured in the same manner as in Example 2.

Figure 3:
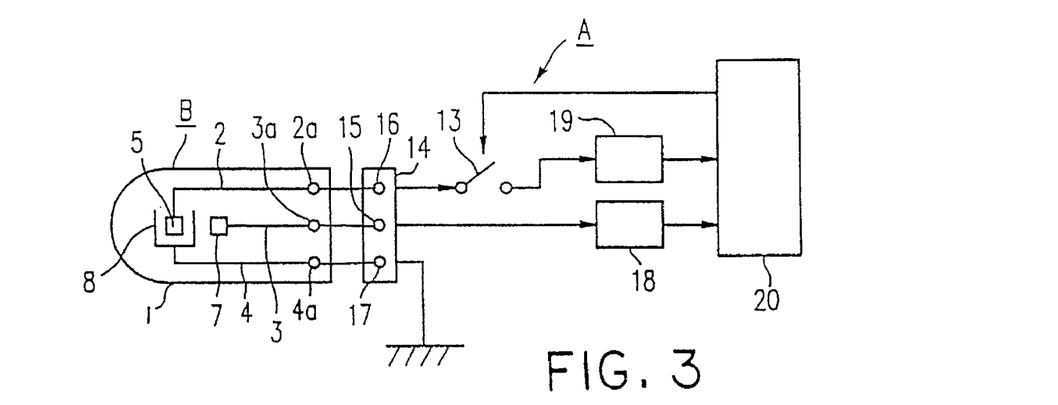
FIG. 3 is a circuit diagram for the biosensor of FIG. 2 and a measuring device connected thereto.

Then, the glucose sensor B was connected to a measuring device A including a circuit as shown in FIG. 3.

The glucose sensor B comprises an electrode system formed on a substrate 1 including a working electrode 5, a counter electrode 8 and a third electrode 7 used for detecting a liquid junction. The working electrode 5 is connected to a terminal 2a via a lead 2, the counter electrode 8 is connected to a terminal 4a via a lead 4, and the third electrode 7 is connected to a terminal 3a via a lead 3.

The measuring device A comprises a connector 14 having terminals 16, 15 and 17 connected to the respective terminals 2a, 3a and 4a of the glucose sensor B, a current detector 18 connected to the terminal 15 of the connector 14, an A/D converting circuit 19 connected to the terminal 16 via a switch 13, and a controller 20 including a microcomputer and the like.

A fixed potential is applied to the terminal 3a. Therefore, when the glucose sensor B is supplied with a sample liquid, a system for detecting the supply of a sample liquid is actuated by detecting a current flowing through the third electrode 7 with the current detector 18. Then, a measurement timer is started by the controller 20.

After a predetermined period of time, for example, after 55 seconds, a fixed voltage required for obtaining a response current is applied between the working electrode 5 and the counter electrode 8 of the glucose sensor B. Then, a current flowing between the working electrode 5 and the counter electrode 8 is converted into a voltage, and the voltage value is converted into the number of pulses in a predetermined period of time by the A/D converting circuit 19. The controller 20 counts up the number of pulses, calculates a response value, and indicates the result.

After a predetermined period of time, a desired potential is applied to the working electrode 5 based on the potential at the counter electrode 8, and a current value 5 seconds after the application is measured. As a result, a current response depending upon the concentration of glucose in the sample liquid is obtained.

In this example, it is also definitely determined whether or not the sample liquid has covered the entire reaction layer as in Example 1. Furthermore, the measurement is not started until the sample liquid reaches the third electrode 7. Accordingly, measurement errors caused by a difference in the amount of a sample liquid can be largely decreased as compared with the measurement by the conventional method.

The above results are also obtained when the third electrode is used as the counter electrode. It is unnecessary, therefore, to distinguish the third electrode from the counter electrode when a voltage is applied for obtaining a sensor response in the measurement as described in Example 3.

Example 4

Figure 4:
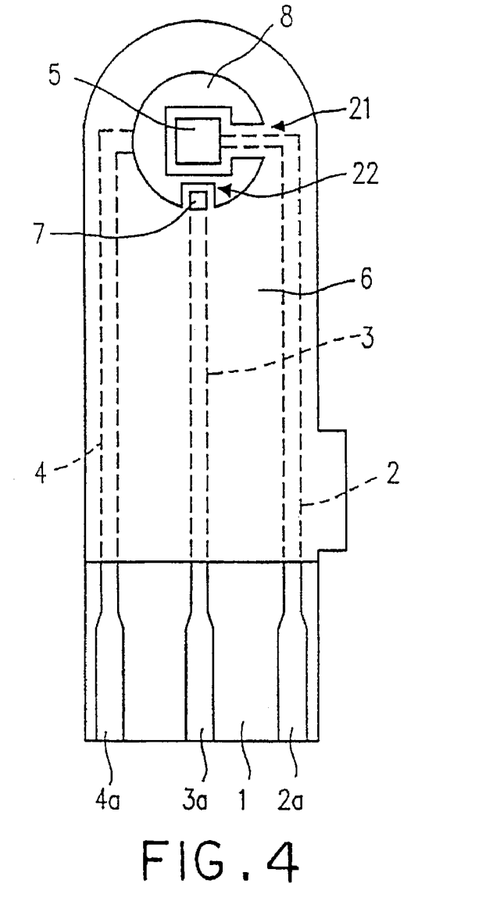
FIG. 4 is a plane view of a substrate having an electrode system used in a glucose sensor as still another example of the biosensor of this invention.

The electrode system of a glucose sensor used in this example is shown in FIG. 4.

In this glucose sensor, a peripheral portion, which is farther from a sample supply port 11, of a substantially C-shaped counter electrode 8 formed on a substrate 1 is opened to provide an electrode receiving portion 22. A third electrode 7 is provided within the electrode receiving portion 22. A reaction layer is formed over not only a working electrode 5 and the counter electrode 8 but also over the third electrode 7. The configuration of this glucose sensor is substantially identical to that of Example 2 except for the above.

The glucose sensor was manufactured in the same manner as in Example 2 except that the reaction layer was formed over the third electrode 7 as well as over the working electrode 5 and the counter electrode 8.

The glucose sensor was supplied with 3 µl of an aqueous solution of glucose as a sample liquid through the sample supply port 11, and a response current value was measured in the same manner as in Example 1. As a result, a current response depending upon the concentration of glucose in the sample liquid was obtained as in Example 1.

In the glucose sensor of this example, the third electrode 7 is formed in the electrode receiving portion 22 provided to the counter electrode 8, and hence, the reaction layer can be easily formed over the third electrode 7. Furthermore, a distance between the working electrode 8 and the third electrode 7 is decreased, resulting in reducing the effect of a voltage decrease in the application of the potential.

Example 5

Figure 5:
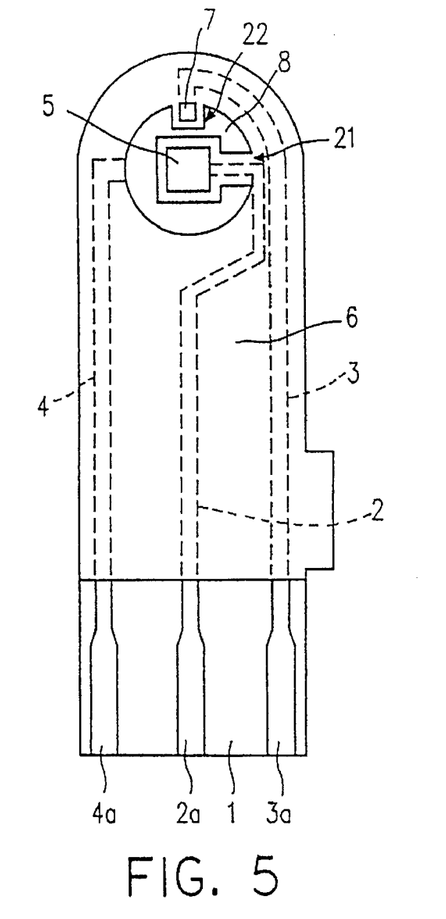
FIG. 5 is a plane view of a substrate having an electrode system used in a glucose sensor as still another example of the biosensor of this invention.

The electrode system of a glucose sensor used in this example is shown in FIG. 5.

In this glucose sensor, a peripheral portion, which is nearer to a sample supply port 11, of a substantially C-shaped counter electrode 8 formed on a substrate 1 is opened to provide an electrode receiving portion 22. A third electrode 7 is provided within the electrode receiving portion 22. A reaction layer is formed over not only a working electrode 5 and the counter electrode 8 but also the third electrode 7. The configuration of this glucose sensor is substantially identical to that of Example 2 except for the above.

The glucose sensor was manufactured in the same manner as in Example 2 except that the reaction layer was formed over the third electrode 7 as well as over the working electrode 5 and the counter electrode 8.

The glucose sensor was provided with 3 µl of an aqueous solution of glucose as a sample liquid through the sample supply port 11, and a response current value was measured in the same manner as in Example 1. As a result, a current response depending upon the concentration of glucose in the sample liquid was obtained as in Example 1.

Furthermore, in the glucose sensor of this example, since the third electrode 7 is formed nearer to the sample supply port 11 on the substrate 1, the third electrode 7 can be soaked with the supplied sample liquid without fail. Therefore, when the third electrode 7 is used as a reference electrode, a reference potential is more stabilized, resulting in less deviation of the response values.

Example 6

Figure 6:
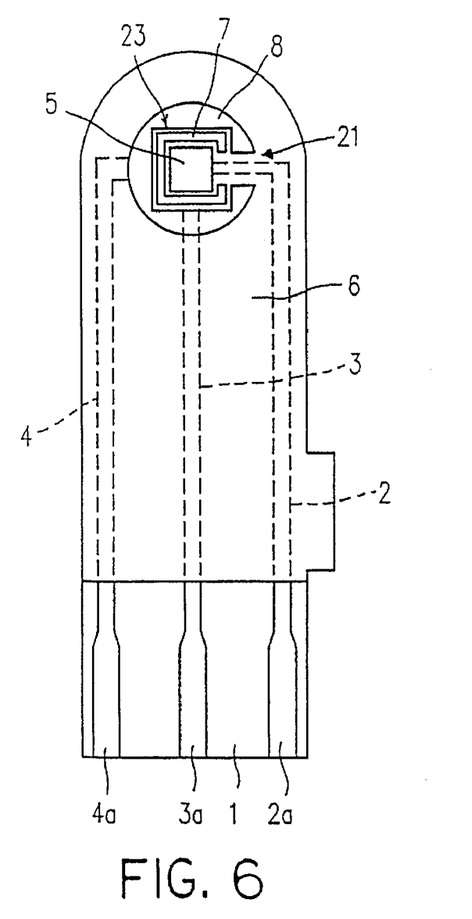
FIG. 6 is a plane view of a substrate having an electrode system used in a glucose sensor as still another example of the biosensor of this invention.

The electrode system of a glucose sensor used in this example is shown in FIG. 6.

In this glucose sensor, a substantially C-shaped counter electrode 8 is provided on a substrate 1, and a working electrode 5 is provided inside of the counter electrode 8. A third electrode 7 is formed in a substantial C-shape within a space 23 between the working electrode 5 and the counter electrode 8. A reaction layer is formed over not only the working electrode 5 and the counter electrode 8 but also the third electrode 7. The configuration of this glucose sensor is substantially identical to that of Example 2 except for the above.

The glucose sensor was manufactured as follows:

Silver paste was printed on the insulating substrate 1 made of polyethylene terephthalate by screen printing, thereby forming leads 2, 3 and 4. Then, conductive carbon paste including a resin binder was printed on the substrate 1, thereby forming the working electrode 5 and the third electrode 7, so that the working electrode 5 be in contact with the lead 2 and the third electrode 7 be in contact with the lead 3.

Next, insulating paste was printed on the resultant substrate 1, thereby forming an insulating layer 6. The insulating layer 6 covered the peripherals of the working electrode 5 and the third electrode 7, thereby exposing fixed areas of the working electrode 5 and the third electrode 7. Furthermore, the insulating layer 6 covered part of the leads 2, 3 and 4.

Then, conductive carbon paste including a resin binder was printed on the resultant substrate 1, thereby forming the counter electrode 8 so as to be in contact with the lead 4.

The manufacturing procedures thereafter were identical to those in Example 4, and the glucose sensor was thus manufactured.

The glucose sensor was supplied with 3 µl of an aqueous solution of glucose as a sample liquid through the sample supply port 11, and a response current value was measured in the same manner as in Example 1. As a result, a current response depending upon the concentration of glucose in the sample liquid was obtained as in Example 1.

Furthermore, in the glucose sensor of this example, since the third electrode 7 is formed at the peripheral of the working electrode 5, the potential application to the working electrode 5 can be more stabilized in using the third electrode 7 as a reference electrode. As a result, the sensor response characteristic is improved.

Example 7

FIG. 7 shows an example of the measuring device according to the present invention. When a microcomputer detects the connection of a biosensor to the measuring device, a predetermined voltage is applied between a third electrode 7 and a counter electrode 8. When a sample liquid is supplied, a current flows between terminals 32 and 33. Upon detection of this electrical change, a controller 28 starts a timer. The application of the predetermined voltage between the third electrode 7 and the counter electrode 8 is kept until the completion of a series of operation. This voltage is not necessarily fixed but may be varied. Thanks to this continuous application of the voltage between the third electrode 7 and the counter electrode 8, no switching component is required between the terminal 32 and the controller 28. This reduces production cost. After a predetermined period of time, a switch 29 is switched on, and a predetermined voltage required for obtaining a response current is applied between a working electrode 5 and the counter electrode 8 or the third electrode 7. A current thus flowing between the working electrode 5 and the counter electrode 8 is converted into a voltage by a current/voltage converting circuit 26, and the obtained voltage value is converted into the number of pulses in a fixed period of time by an A/D converting circuit 27. The controller 28 counts up the number of the pulses, calculates a response value, and indicates the result.

The voltage for detecting a liquid junction was 0.5V, whereas the voltage for obtaining a sensor response was 0.5V for the application between the working electrode 5 and the counter electrode 8. No influence to the sensor response is observed by the continuous application of the voltage for detecting a liquid junction.

Example 8

FIG. 8 shows another measuring device according to the present invention. The measuring device is provided with a switch 29 which can be switched between terminals 31 and 32 of a connector 25. The switch 29 is kept connected to the terminal 32 through the detection of the supply of a sample liquid until immediately before the application of a fixed voltage required for obtaining a response current between a working electrode 5 and a counter electrode 8 or a third electrode 7. During this time, a predetermined voltage may be continuously applied between the third electrode 7 and the counter electrode 8. By using the switch 29 switchable between the terminals 31 and 32, a common circuit can be used for a current/voltage converting circuit and an A/D converting circuit. This reduces production cost. After a predetermined period of time, the switch 29 is switched to the terminal 31, and a fixed voltage required for obtaining a response current is applied between the working electrode 5 and the counter electrode 8.

The voltage for detecting a liquid junction was 0.5V, whereas the voltage for obtaining a sensor response was 0.5V for the application between the working electrode 5 and the counter electrode 8. No influence to the sensor response is observed by the continuous application of the voltage for detecting a liquid junction.

The voltages for detecting a liquid junction and for obtaining a sensor response are not limited to 0.5V as used in Examples 7 and 8. Any voltage which allows the detection of an electrical change between the third electrode 7 and the counter electrode 8 can be used as the voltage for detecting a liquid junction. Also, any voltage which allows the oxidation of a reduced form of an electron acceptor resulted from a series of reactions can be used as the voltage for obtaining a sensor response.

In the above examples, the positions, shapes, sizes, and the like of the electrodes, leads, etc. can be changed arbitrarily.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed:

1. A method for quantifying a substrate in a sample liquid by using a biosensor comprising:
   an electrically insulating substrate;
   an electrode system formed on the substrate including a working electrode, a counter electrode and a third electrode used for detecting a liquid junction; and
   a reaction layer that is formed over at least the working electrode and the counter electrode of the electrode system and includes an oxidoreductase;
   wherein the method of quantifying the substrate comprises the steps of:
      applying a voltage between the counter electrode and the third electrode;
      supplying a sample liquid to the reaction layer;
      detecting an electrical change between the counter electrode and the third electrode caused by supplying the sample liquid to the reaction layer;
      applying a voltage between the working electrode and both of the third electrode and the counter electrode after detecting the electrical change; and
      measuring a current flowing between the counter electrode and the working electrode after applying the voltage.

2. A method for quantifying a substrate according to claim 1, wherein the step of applying a voltage between the counter electrode and both of the third electrode and the counter electrode is conducted while a voltage is continuously applied between the counter electrode and the third electrode.

3. A method for quantifying a substrate in a sample liquid by using a biosensor comprising:
   an electrically insulating substrate;
   an electrode system formed on the substrate including a working electrode, a counter electrode and a third electrode used for detecting a liquid junction; and
   a reaction layer that is formed over at least the working electrode and the counter electrode of the electrode system and includes an oxidoreductase;
   wherein the method of quantifying the substrate comprises the steps of:
      applying a voltage between the counter electrode and the third electrode;
      supplying a sample liquid to the reaction layer;
      detecting an electrical change between the counter electrode and the third electrode caused by supplying the sample liquid to the reaction layer;
      applying a voltage between the working electrode and the counter electrode after detecting the electrical change; and
      measuring a current flowing between the counter electrode and the working electrode after applying the voltage.

4. A method for quantifying a substrate according to claim 3, wherein the step of applying a voltage between the working electrode and the counter electrode is conducted while a voltage is continuously applied between the counter electrode and the third electrode.

5. A quantifying device for a substrate contained in a sample liquid comprising:
   a biosensor comprising: an electrically insulating substrate;
   an electrode system formed on the substrate including a working electrode, a counter electrode and a third electrode used for detecting a liquid junction; and
   a reaction layer that is formed over at least the working electrode and the counter electrode of the electrode system and includes an oxidoreductase;
   wherein the quantifying device additionally comprises:
      means for detecting an electrical change between the counter electrode and the third electrode caused by supplying a sample liquid to the reaction layer;
      means for applying a voltage between the working electrode and both of the third electrode and the counter electrode after detecting the electrical change; and
      means for measuring a current flowing between the working electrode and the counter electrode.

6. A quantifying device according to claim 5, wherein the means for applying a voltage between the working electrode and both of the third electrode and the counter electrode applies the voltage while a voltage is continuously applied between the counter electrode and the third electrode.

7. A quantifying device for a substrate contained in a sample liquid comprising:
   a biosensor comprising:
      an electrically insulating substrate;
      an electrode system formed on the substrate including a working electrode, a counter electrode and a third electrode used for detecting a liquid junction; and
      a reaction layer that is formed over at least the working electrode and the counter electrode of the electrode system and includes an oxidoreductase;
      wherein the quantifying device additionally comprises:
         means for detecting an electrical change between the counter electrode and the third electrode caused by supplying a sample liquid to the reaction layer;
         means for applying a voltage between the working electrode and the counter electrode after detecting the electrical change; and
         means for measuring a current flowing between the working electrode and the counter electrode.

8. A quantifying device according to claim 7, wherein the means for applying a voltage between the working electrode and the counter electrode applies the voltage while a voltage is continuously applied between the counter electrode and the third electrode.

9. A quantifying device for a substrate contained in a sample liquid, comprising a biosensor comprising:
   an electrically insulating substrate;
   an electrode system formed on the substrate including a working electrode, a counter electrode and a third electrode used for detecting a liquid junction; and
   a reaction layer that is formed over at least the working electrode and the counter electrode of the electrode system and includes an oxidoreductase;
   wherein the quantifying device additionally comprises a measuring device to which the biosensor is removably connected, wherein the measuring device includes:
current/voltage converting circuits connected to the third electrode of the biosensor; A/D converting circuits connected to the current/voltage converting circuits; current/voltage converting circuits which connects the working electrode of the biosensor via a switch; A/D converting circuits connected to the current/voltage converting circuits; and a controller connected to the respective A/D converting circuits, the switch being turned ON or OFF with respect to the working electrode by a control of the controller, and wherein an electrical change between the counter electrode and the third electrode, caused by a supply of a sample liquid to the reactive layer, is detected by the control portion under a condition that the switch is insulated from the working electrode, and then a voltage is applied between the working electrode and both of the third electrode and the counter electrode under a condition that the switch is connected to the working electrode and a current flowing between the working electrode and the counter electrode is measured.

10. A quantifying device according to claim 9, wherein the application of a voltage between the working electrode and both of the third electrode and the counter electrode is conducted while a voltage is continuously applied between the counter electrode and the third electrode.

11. A quantifying device for a substrate contained in a sample liquid, comprising a biosensor comprising:
an electrically insulating substrate;
an electrode system formed on the substrate including a working electrode, a counter electrode and a third electrode used for detecting a liquid junction; and
a reaction layer that is formed over at least the working electrode and the counter electrode of the electrode system and includes an oxidoreductase;
wherein the quantifying device additionally comprises a measuring device to which the biosensor is removably connected,
wherein the measuring device includes:
current/voltage converting circuits connected to the third electrode of the biosensor; A/D converting circuits connected to the current/voltage converting circuits; current/voltage converting circuits which connects the working electrode of the biosensor via a switch; A/D converting circuits connected to the current/voltage converting circuits; and a controller connected to the respective A/D converting circuits, the switch being turned ON or OFF with respect to the working electrode by a control of the controller, and wherein an electrical change between the counter electrode and the third electrode, caused by a supply of a sample liquid to the reactive layer, is detected by the control portion under a condition that the switch is insulated from the working electrode, and then a voltage is applied between the working electrode and the counter electrode under a condition that the switch is connected to the working electrode and a current flowing between the working electrode and the counter electrode is measured.

12. A quantifying device according to claim 11, wherein the application of a voltage between the working electrode and the counter electrode is conducted while a voltage is continuously applied between the counter electrode and the third electrode.

13. A quantifying device for a substrate contained in a sample liquid, comprising a biosensor comprising:
an electrically insulating substrate;
an electrode system formed on the substrate including a working electrode, a counter electrode and a third electrode used for detecting a liquid junction; and
a reaction layer that is formed over at least the working electrode and the counter electrode of the electrode system and includes an oxidoreductase;
wherein the quantifying device additionally comprises a measuring device to which the biosensor is removably connected,
wherein the measuring device includes:
current/voltage converting circuits switchably connected to the third electrode of the biosensor and the working electrode; A/D converting circuits connected to the current/voltage converting circuits; a controller connected to the respective A/D converting circuits, the switch being alternatively connected to the working electrode and the third electrode by a control of the controller, and
wherein an electrical change between the counter electrode and the third electrode, caused by a supply of a sample liquid to the reactive layer, is detected by the control portion under a condition that the switch is connected to the third electrode, and then a voltage is applied between the working electrode and the counter electrode under a condition that the switch is connected to the working electrode and a current flowing between the working electrode and the counter electrode is measured.

* * * * *